(12) United States Patent
Tijsterman

(10) Patent No.: US 9,982,226 B2
(45) Date of Patent: May 29, 2018

(54) DISCONTINUOUS FED BATCH PROCESSING WITH THE USE OF ALTERNATING BIOREACTORS

(71) Applicant: BIOSANA PTY LTD, Eveleigh (AU)

(72) Inventor: Jacob Arthur Tijsterman, Haarlem (NL)

(73) Assignee: BIOSANA PTY LTD, Eveleigh (AU)

( * ) Notice: Subject to any disclaimer, the term of this patent is extended or adjusted under 35 U.S.C. 154(b) by 0 days. days.

(21) Appl. No.: 14/441,818

(22) PCT Filed: Nov. 8, 2013

(86) PCT No.: PCT/NL2013/050805
§ 371 (c)(1),
(2) Date: May 8, 2015

(87) PCT Pub. No.: WO2014/073967
PCT Pub. Date: May 15, 2014

(65) Prior Publication Data
US 2015/0299644 A1    Oct. 22, 2015

(30) Foreign Application Priority Data

Nov. 9, 2012    (WO) ................ PCT/NL2012/050798

(51) Int. Cl.
*C12M 1/00*    (2006.01)
*C07K 16/00*    (2006.01)
*C12M 1/34*    (2006.01)

(52) U.S. Cl.
CPC ............ *C12M 47/10* (2013.01); *C07K 16/00* (2013.01); *C12M 23/58* (2013.01); *C12M 29/00* (2013.01); *C12M 29/04* (2013.01); *C12M 29/18* (2013.01); *C12M 41/46* (2013.01)

(58) Field of Classification Search
None
See application file for complete search history.

(56) References Cited

U.S. PATENT DOCUMENTS

2006/0216790 A1*  9/2006  Knudsen ................ C12M 41/34
                                                          435/69.6
2013/0309757 A1* 11/2013  Kim ....................... C12M 47/06
                                                          435/257.3

FOREIGN PATENT DOCUMENTS

| WO | WO-86/00339 | 1/1986 | | |
|---|---|---|---|---|
| WO | WO-89/08701 | 9/1989 | | |
| WO | WO-2005/007269 | 1/2005 | | |
| WO | WO-2009/023562 | 2/2009 | | |
| WO | WO-2009/131659 | 10/2009 | | |
| WO | WO 10/008579 | * 1/2010 | ............. | C12M 1/40 |
| WO | WO-2011/062926 | 5/2011 | | |
| WO | WO 12/081931 | * 6/2012 | ................ | C12P 1/00 |

OTHER PUBLICATIONS

International Search Report for PCT/NL2013/050805, dated Jan. 27, 2014, 3 pages.

* cited by examiner

*Primary Examiner* — Allison M Fox
(74) *Attorney, Agent, or Firm* — Morrison & Foerster LLP

(57) ABSTRACT

The present invention relates to discontinuous fed batch cell culturing of mammalian cells (more specific CHO cells) with the use of alternating bioreactors in combination with discontinuous separation of biomass from biological substance (more specific monoclonal antibodies) and waste components.

8 Claims, 3 Drawing Sheets

1

DISCONTINUOUS FED BATCH PROCESSING WITH THE USE OF ALTERNATING BIOREACTORS

CROSS-REFERENCE TO RELATED APPLICATIONS

This application is the national phase of PCT application PCT/NL2013/050805 having an international filing date of 8 Nov. 2013, which claims benefit of PCT patent application No. PCT/NL2012/050798 filed 9 Nov. 2012. The contents of the above patent applications are incorporated by reference herein in their entirety.

The invention relates to methods and systems that are used for the large scale culture of cells, particularly suspension cells.

The culturing of cells can be done on a laboratory scale or industrial scale. The two scales provide different challenges to the users. What works on a laboratory scale very often does not work on a large scale. A main difference is the efficiency of the culture process.

The present invention is in particular concerned with large scale fed-batch culture or fermentation. There are two basic approaches to the fed-batch fermentation; the constant volume fed-batch culture and the variable volume fed-batch culture.

In fixed volume fed-batch, the limiting substrate is fed without diluting the culture. The culture volume can also be maintained practically constant by feeding the growth limiting substrate in undiluted form, for example, as a very concentrated liquid or gas (ex. oxygen). A certain type of extended fed-batch—the cyclic fed-batch culture for fixed volume systems—refers to a periodic withdrawal of a portion of the culture and use of the residual culture as the starting point for a further fed-batch process. Basically, once the fermentation reaches a certain stage, (for example, when aerobic conditions cannot be maintained anymore) part of the culture is removed and the remaining biomass is diluted to the original volume with sterile water or medium containing the feed substrate. The dilution decreases the biomass concentration and typically results in an increase in the specific growth rate. Subsequently, as feeding continues, the growth rate will decline gradually as biomass increases and approaches the maximum sustainable in the vessel once more, at which point part of the culture may again be replaced by fresh culture medium.

A variable volume fed-batch is one in which the volume changes with the fermentation time. The reason for the change is typically the substrate feed. The way this volume changes it is dependent on the requirements, limitations and objectives of the operator. This type of fed-batch can still be further classified as repeated fed-batch process or cyclic fed-batch culture, and single fed-batch process. The former typically implies that once the fermentation reached a certain stage after which is not effective anymore, a quantity of culture is removed from the vessel and replaced by fresh nutrient medium. The decrease in the cell numbers results in an increase in the specific growth rate, followed by a gradual decrease as the quasi-steady state is established.

Fed-batch fermentation has characteristics of batch-wise production as well as continuous fermentation. Fed-batch offers several advantages over batch and continuous cultures. The feed of the required components for growth and/or other substrates required for the production of the product is not depleted and the nutritional environment can be maintained approximately constant during the course of the batch. The production of by-products that are generally related to the presence of high concentrations of substrate can also be avoided by limiting its quantity to the amounts that are required solely for the production of the product.

A cyclic fed-batch culture has the additional advantage that the productive phase of the process may be extended under controlled conditions. The controlled periodic shifts in growth rate provide an opportunity to optimize product synthesis, particularly if the product of interest takes place during the deceleration in growth.

DISCLOSURE OF THE INVENTION

A problem associated with the production of biological substances using culture systems is the relatively high costs associated with the production of the biological substance. The present invention provides for a more efficient culture system. The present invention allows for the cost-effective and controlled production of a biological substance.

In one embodiment the invention provides a method for the production of a biological substance by culturing cells that produce said biological substance in a bioreactor, said method comprising:

providing a bioreactor with a cell culture comprising said cells suspended in a culture medium;

said method further comprising performing at least one culture and harvest cycle comprising incubating said cell culture in a bioreactor until it has reached the early stationary, or stationary phase, and harvesting the culture medium with the biological substance by separating the cells from the culture medium containing the biological substance and feeding essentially all cells back into a bioreactor for continued culture together with fresh culture medium. An advantage of a method of the invention is the high yield of the biological substance. The yield of substance is further increased with each further incubation/culture and harvest cycle. Thus preferably a method of the invention comprises at least 2, more preferably at least 5, more preferably at least 10 and preferably at least 20 incubation and harvest cycles.

The cell culture is harvested with a harvest system that preferably maintains many of the conditions of the incubation step. The harvest system therefore preferably comprises means for maintaining the culture temperature. When the volume of the cell culture in the bioreactor exceeds the capacity of the harvest system the entire cell culture can still be harvested. Preferably this is done by sequentially feeding aliquots of the cell culture to the harvest system. The harvest cycle is then completed when essentially the entire cell culture is processed. The cell culture that is waiting to be processed is not mixed with cells that have already been processed by the harvest system. This is achieved by feeding the processed cells into a different bioreactor. The processed cells are therefore provided with fresh medium and fed into the different bioreactor for the subsequent incubation and harvest cycle. The cell density can be adjusted at this stage, if so desired. The cells can be concentrated or diluted, depending on the wishes of the operator. It is an advantage of the present invention that it is possible to implement a harvest system that has a lower capacity than the volume of the cell culture.

An increase in the cell density is desirably, particularly in the first cycles, to quickly obtain the target cell density that is desired for production of the biological substance. Dilution is typically desired in later cycles to accommodate the continued increase in the number of cells.

DETAILED DESCRIPTION OF THE INVENTION

Figure 1:
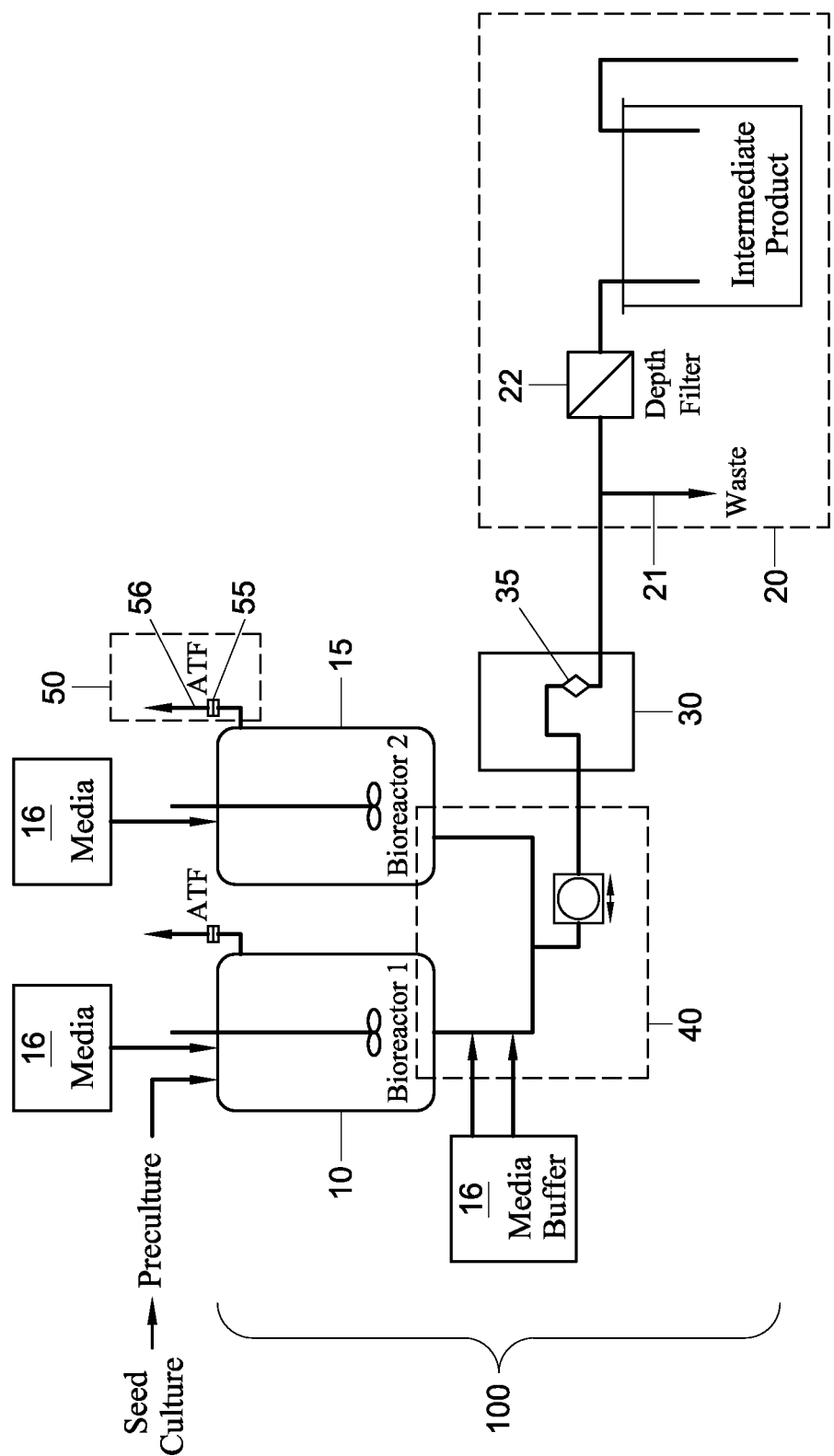
FIG. 1 illustrates a harvest system, comprising a plurality of bioreactors.

The biological substance is preferably a substance that is excreted from the cells. The biological substance is preferably a protein, preferably an excreted protein. The protein preferably comprises more than 50, and preferably more than 100 amino acids. In a particularly preferred embodiment the biological substance is a growth factor, an antibody or a soluble form of a membrane bound ligand. The biological substance can also comprise an antigen binding fragment of an antibody. Non-limited examples of such fragments are single chain Fv fragments, FAB-fragments, monovalent antibodies and heavy chain only antibodies. In a preferred embodiment the antibody is a mammalian antibody. In a preferred embodiment the antibody is a monoclonal antibody. In a preferred embodiment the antibody is a mouse, human or mouse/human chimeric antibody. The chimeric antibody is preferably a humanized murine monoclonal antibody or human antibody. Various types of humanization exist. Typically at least the constant parts of the antibody are human. Modern humanized antibodies also contain human variable regions wherein CDR regions are replaced by the murine CDRs. Alternatively, the antibody contains mutations in the murine variable regions to remove predicted human B and/or T cells epitopes. Presently it is possible to generate so-called fully human monoclonal antibodies. These are generated completely from human sequences. Immune response to these fully human antibodies are nevertheless still possible depending on the way of administration and the nature of the CDRs.

Cells can be grown either in suspension or adherent cultures. Some cells naturally live in suspension, without being attached to a surface, such as cells that exist in the bloodstream. There are also cell lines that have been modified to be able to survive in suspension cultures so they can be grown to a higher density than adherent conditions would allow. Adherent cells require a surface, such as tissue culture plastic or microcarrier, which may be coated with extracellular matrix components to increase adhesion properties and provide other signals needed for growth and differentiation. Adherent cells can typically be adapted to suspension growth, alternatively the cells can, as mentioned above, be adhered to microcarriers that are subsequently suspended and cultured in the bioreactor. The cells in the present invention are preferably cells that grow in suspension. Mammalian cells are preferred. Preferred production cells are the Chinese hamster ovary or CHO cells and the NSO cell line. In a particularly preferred embodiment the cells are CHO cells.

Cell growth in a typical fed-batch culture of mammalian cells can be classified into 7 stages: (A) lag phase; (B) early log phase; (C) log/exponential phase; (D) Early Stationery phase; (E) stationary phase; (G) Early Death phase (F) Death phase.

A. During lag phase, the cells adapt themselves to growth conditions. The cell numbers in the population do not increase.

B. During early log phase more and more cells have adapted and are entering the exponential phase.

C. Exponential phase (sometimes called the log phase or the logarithmic phase) is a period characterized by cell doubling. The number of new cells appearing per unit time is proportional to the present population. If growth is not limited, doubling will continue at a constant rate so both the number of cells and the rate of population increase doubles with each consecutive time period. For this type of exponential growth, plotting the natural logarithm of cell number against time produces a straight line. The slope of this line is the specific growth rate of the cells. The actual rate of this growth (i.e. the slope of the line in the figure) depends upon the growth conditions and the type of cells.

D. Early stationary phase (or early plateau phase) is the phase between the log-phase and stationary phase and is characterised by a progressive decline in the rate of population increase. This phase is characterised in that the growth rate of the population is a third or less from the maximum growth rate in the exponential phase. The early stationary phase ends when growth of the cell population is zero or less.

E. The stationary phase or plateau phase is often due to a growth-limiting factor; this is mostly depletion of a nutrient, and/or the formation of inhibitory products. In the stationary phase the size of the cell population remains more or less constant. Biological substance production is typically highest in this phase.

F. In the death phase, the cells run out of nutrients, or toxic products have build up to such an extend that the cells die.

G. The early death phase defines the end of the stationary phase when more and more cells die.

Depending on how the cells have been treated prior to initiating the culture the lag phase can be present or absent. For instance, large scale cultures are typically initiated from seed cultures and pre-cultures. In such cases it is possible to have a very short or absent lag phase, as the cells can have already adapted to the culture conditions in the fed-batch culture in an appropriate seed and/or pre-culture.

In cyclic culture systems, such as the present invention, the later cycles typically repeat the stages C and D. Optionally one or more of the cycles include in addition the steps E, F and G. The exponential phase in later cycles may or may not reach the same maximum growth rate as the first cycle. In each cycle the start of the early stationary phase is characterised in that the growth rate of the population declines to a third or less from the maximum growth rate in the previous exponential phase. The growth rate is typically calculated from the tangent line of the growth curve.

In a particularly preferred embodiment the culture for each cycle is harvested while the culture is in stage C, D or E. Preferably the culture for each cycle is harvested while the culture is in stage C or D, more preferably at stage D.

In another embodiment the culture in cycles 2 and further is harvested after at least one day, preferably at least two days, more preferably at least three days of incubation, irrespective of the stage of the stage of growth the cells are in at the time of initiation of the harvest step.

In another embodiment the culture for each cycle is harvested when a predetermined cell density has been reached. For cultures after the first culture and harvest cycle, it is preferred that the culture is harvested when the cells in the culture have reached a cell density of at least $0.7 \times 10e8$, preferably at least $1 \times 10e8$ and more preferably at least $2 \times 10e8$ per ml.

Figure 2:
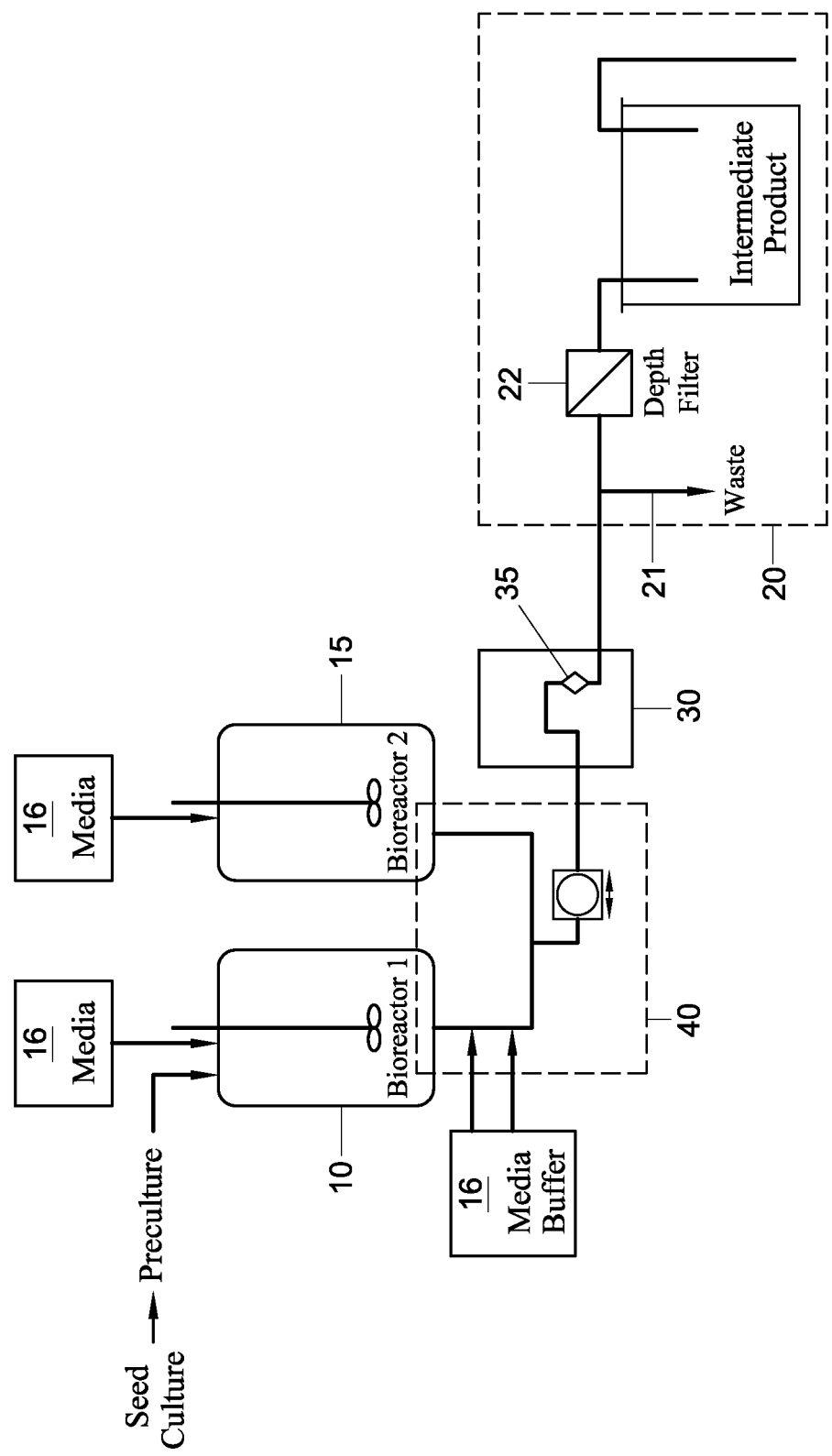
FIG. 2 illustrates a harvest system, comprising a plurality of bioreactors without alternating tangential flow filtration devices (or ATF).
Figure 3:
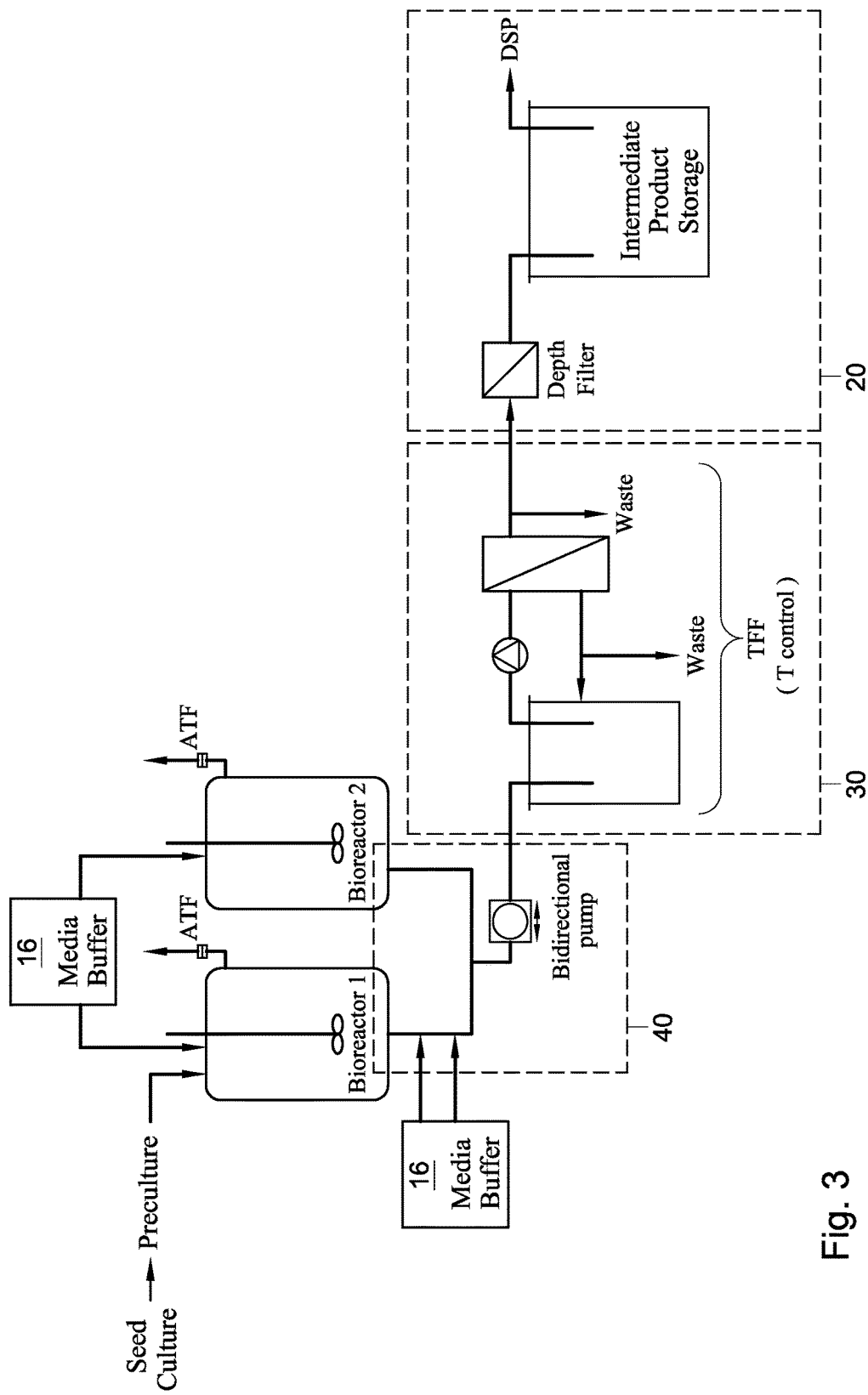
FIG. 3 illustrates a separator, showing a tangential flow filtration module.

Examples of systems for the production of a biological substance are given in the FIGS. 1-3. In the systems, cells that produce said biological substance are cultured and are separated from a culture medium containing the biological substance. After separation, preferably essentially all cells are fed back into a bioreactor for continued culture together with fresh culture medium. In FIG. 1 a harvest system 100 comprises a plurality of bioreactors 10, 15. The bioreactors are arranged to incubate a cell culture of cells suspended in a culture medium in said bioreactor. The system is comprised of a number of culture medium feeds (16) arranged to compensate effluent loss by feeding culture medium or a component thereof into the bioreactors.

In particular, a feed 16 is directly coupled to the bioreactor, wherein another feed 16 for feeding media and buffer can be coupled to a pump and switching unit 40, that connects to a separator 30.

In addition, means are provided (not shown) for detecting a cell count or density in the bioreactors 10, 15. Typically, such means may be a cell count detector, density meter or flow cytometer, of a type known in the art. The detector can be arranged to detect a cell density. A predetermined threshold value can be determined heuristically or by means of a calculation for inputting to the detector, indicating that incubation of a cell culture in one of said bioreactors has reached the early stationary phase or stationary phase as hereabove clarified.

Separator 30 is arranged communicatively coupled between a harvesting filter module 20 and the plurality of bioreactors. The separator is fed by the cell culture that is pumped, by the pump and switching unit, out of one of the bioreactors 10, 15, and is further fed by a medium and buffer feed 16. In the example of FIGS. 1 and 2, the separator 30 is arranged to separate the cells from the culture medium containing the biological substance by means of a centrifuge 35. In the centrifuge 35, a concentrated fluidized bed of cells is formed by a balancing the fluid flows of the fresh medium 16, the cell feed from the bioreactor and the rotational speed of the centrifuge 35 through the continuous balanced action of centrifugal and fluid flow forces, known per se.

The centrifuge 35 comprises an inlet of fresh medium 16 arranged to provide said fluid flow force thereby separating the cells from the culture medium with the biological substance.

In the example, the pump and switching unit 40 are formed by a bidirectional pump, coupled to switches that switch a fluid flow between one of the bioreactors 10 and the other bioreactor 15 after clarifying the cell culture in separator 35. In use, upon detection of said early stationary phase or stationary phase in one of said plurality of bioreactors 10, 15, a flow is generated to the separator 30 by extracting the cell culture from one of the bioreactors 15 and feeding the separator with fresh medium and buffer.

By directing the flow back from the separator and switching the flow towards the other bioreactor 15, essentially all cells are fed back from the separator 30 via said pump and switching unit 40, into the other one 15 bioreactor for continued culture together with fresh culture medium.

The culture medium containing the biological substance and buffer are periodically fed into the harvesting module 20 that harvests the biological substance by filtration as further described herein below.

Cultures can reach higher cell densities during incubation when the medium is at least in part recycled. Thus during incubation of the cell culture, in contrast to the system disclosed in FIG. 2, preferably at least part of the cell culture of bioreactors 10 and 15 is continuously flowed into a separation system 50 that comprises a size selective semi-permeable membrane 55.

The membrane 55 separates the cells and the biological substance from substances having a lower molecular weight than the biological substance, thereby creating a cell- and biological substance-free effluent that is outputted. In addition, a cell- and biological substance-containing fluid stream is fed back into the bioreactor, and effluent loss is at least compensated by feeding culture medium or a component thereof into the bioreactor.

Such membrane separation devices 50 are often referred to as alternating tangential flow filtration devices (or ATF). This type of filtration is different from dead-end filtration in which the feed is passed through a membrane or bed, the solids being trapped in the filter and the filtrate being released at the other end. In ATF filtration the majority of the feed flow travels tangentially across the surface of the filter, rather than into the filter. The alternating tangential flow is created by the action of a diaphragm moving upwards and downwards within a pumphead, connected to a filterhousing and attached to a bioreactor (see for reference WO2005/095578 and WO2008/006494).

The membrane separation device 50 is typically an ultrafiltration device. The filter in the separation device is typically a semi permeable membrane comprising pores with a certain molecular weight cut-off. The filter or semi-permeable membrane used in the process of the invention is capable of separating the biological substance from substances having a lower molecular weight than the biological substance. In other words, the molecular weight cut-off is chosen such that the molecular weight cut-off (MWCO) is smaller than, more preferably at least a factor 2, most preferably at least a factor 3 smaller than the molecular weight of the biological substance. Typically, but of course depending on the molecular weight of the biological substance produced in the process of the present invention, the MWCO of the separation system is preferably at least 5, more preferably at least 10, most preferably at least 3 0kDa and preferably at most 500 kDa, more preferably at most 300 kDa, most preferably at most 10 0kDa. For example for an IgG with a molecular weight of 15 0kDa, a separation system having a MWCO of at most 5 0kDa is most preferred.

The harvesting step of the incubation and harvest cycle is performed on the entire culture. In the present invention it is preferred that the culture volume is higher than the capacity of the harvest device. In this embodiment the harvesting is done by sequentially feeding the culture into the harvest system. The harvest system preferably comprises a cross-flow filtration system, whereby the medium with the biological substance is replaced by fresh culture medium. Such cross-flow harvest system typically contains filters or semi-permeable membranes with an MCWO that separates cells from the biological substance and the culture medium. In these devices the MCWO is typically higher than 200 kDa. Such devices are also referred to as cross-flow microfiltration devices and the methods as micro-filtration. In these microfiltration devices the pore size is typically between 0.1 micrometer till 10 micrometer.

In a particularly preferred embodiment the harvest system comprises a centrifugal force based fluidized bed system. In this embodiment a method of the invention it is preferred that the culture medium with the biological substance is harvested by flowing the cell culture into a centrifuge that maintains the cells as a concentrated fluidized bed through the continuous balanced action of centrifugal and fluid flow forces, whereby the fluid flow force is applied by the inflow of fresh medium thereby separating the cells from the culture medium with the biological substance. Preferred examples of centrifugal force based fluidized bed systems are described in WO10/008579, WO10/008563 and WO11/044237. These references are therefore incorporated by reference herein.

By way of contrast, FIG. 3 illustrates a separator 30, showing a tangential flow filtration module. In the module, similar to the membrane separation device 50 described hereabove a size selective semipermeable membrane is provided and an inlet of fresh medium is arranged to provide tangential flow. Here the size selective semipermeable membrane is designed to retain the cells and allow the medium together with the biological substance to be collected in the effluent. In this way the cells are separated from the culture medium with the biological substance and essentially all cells can be fed back into another bioreactor 15 for continued culture together with fresh culture medium.

A large scale culture according to the present invention is a culture that comprises at least 1 liter and preferably at least 2 liter of culture medium and cells per incubation and harvest cycle. Preferably it comprises at least 5 liter of culture medium and cells.

A method of the invention preferably comprises a fed-batch culture system as the incubation step in the incubation and harvest cycles.

When the cell culture incubation in subsequent culture and harvest cycles was performed in different or alternating bioreactors, it was surprisingly observed that the cell cultures developed faster and yielded more biological product. This was particularly so for embodiments wherein the volume of the culture (i.e. culture medium and cells), exceeded the capacity of a single run of the harvest system. Higher yields where seen when the cells collected where transferred to a different bioreactor. This led to a preferred method of operation wherein the cell culture is transferred to a different bioreactor for each incubation and harvest cycle. In this embodiment it is preferred that the culture alternates between two bioreactors for each incubation and harvest cycle. This leads to the situation that, during harvesting, culture is inputted into the harvest system from one bioreactor, is processed in the harvest system, and subsequently the cells in fresh culture medium are outputted to the other bioreactor. A used bioreactor can remain in the system as is, to receive the culture upon completion of the next cycle, it can be cleaned or it can be replaced by a clean bioreactor, or a combination thereof.

In a preferred embodiment the invention comprises discontinuous fed batch cell culturing of mammalian cells (more specific CHO cells) with the use of alternating bioreactors in combination with discontinuous separation of biomass from biological substance (more specific monoclonal antibodies) and waste components.

High cell density, high cell viability and high productivity can discontinuously be maintained in time by separating biomass in the early stationary growth phase from biological substance and waste components and reintroducing these viable cells into a second bioreactor that is operated in the fed batch mode. The cells will then continue to grow in the exponential phase and reach the early stationary phase (often within 0.5-2 days). Hereafter the discontinuous separation process is repeated and biomass transferred back to the first reactor that is operated in fed batch mode and again the cells are grown for 0.5-2 days from the exponential phase to the early stationary phase. This process of discontinuous fed batch in alternating bioreactors after separation of biological substance and waste components is repeated until sufficient biological substance has been obtained or cell viability falls below 90%. If required, biomass can be concentrated or diluted after separation before transfer to the next bioreactor.

The preferred embodiment of the invention wherein during incubation of the cell culture in the bioreactor at least part of the cell culture is continuously flowed into a separation system that comprises a size selective membrane is preferably combined with the preferred embodiment wherein the culture medium with the biological substance is harvested by flowing the cell culture into a centrifuge that maintains the cells as a concentrated fluidized bed through the continuous balanced action of centrifugal and fluid forces, whereby the fluid force is applied by fresh medium thereby separating the cells from the culture medium with the biological substance. The cells can subsequently be transferred back into the bioreactor for a further culture and harvest cycle, or be transferred into another bioreactor. With the latter setup, as mentioned herein above, it is possible to implement a harvest system that has a lower fluid capacity than the volume of the cell culture. In the further incubation it is preferred that at least part of the cell culture is continuously flowed into a separation system that comprises a size selective membrane. In the separation device consumed medium and substances (waste) with a lower molecular weight than the biological substance are removed from the culture. In the harvest system consumed medium, the biological substance and substances (wastes) having a higher molecular weight than the biological substance, such as cell debris, nucleic acids, and proteins are removed from the culture. This preferred embodiment is a particularly effective way in providing the conditions for multiple culture and harvest cycles at very high cell densities, while maintaining a relatively low cost system associated with the continuous culture in a bioreactor wherein at least part of the cell culture is continuously flowed into a separation system that comprises a size selective membrane.

It is preferred that culture conditions during culture are maintained in the separation system and the centrifuge. In this way the cells that are cultured experience culture conditions throughout the various culture and harvest cycles of the present invention. From the viewpoint of the cells, the culture is a continuous culture, whereas from a viewpoint of the process operator in charge of handling the waste disposal and harvesting of the biological substance, the culture is semi-continuous. From the viewpoint of the cells the system comprising the separation system, the centrifuge and the one or more bioreactors can be seen as one bioreactor for the culture of the cells. The cells experience culture conditions throughout the procedure. Not all culture conditions have to be maintained. A preferred culture condition to maintain is the temperature, another culture condition that is preferably maintained is oxygenation. Yet a further culture condition that is preferably maintained is the pH. Maintenance of a culture condition preferably means that the condition throughout the procedure does not deviate more than 15% from the value of the condition at the start of the procedure. Temperature is preferably maintained at 35.5-37.5° C., preferably at 37 C, oxygenation is preferably maintained at 40-60% expressed as dissolved oxygen concentration, preferably at 50% dissolved oxygen concentration, pH is preferably maintained at a value of pH 6.7-7.5, preferably at pH 7 or 7.1.

In one embodiment it is preferred that in the first of the culture and harvest cycles, the cells are harvested at a lower cell density than in the later culture and harvest cycles. In this embodiment the cells are harvested preferably at a cell density of less than 50×10e6, preferably less than 25×10e6 cells/ml.

The cell density of the cells in the culture medium that is outputted from the centrifuge step, in the harvest step can be altered with respect to the cell density of the cells in the culture medium that is inputted into the centrifuge. This embodiment allows for the setting of the cell density of the cells in the culture medium at the start of the culture in the next culture and harvest cycle. Depending on the desired or required cell density the use of an ATF apparatus can be applied to both bioreactors with an adjusted feed strategy. Separation of biological substance and waste components (the interstitial fluid) is realized by the use of centrifugation or cross-flow filtration in a harvesting filter module 20. To this end, in the FIGS. 1-3 harvesting filter module 20 comprises a waste outlet 21 and a depth filter 22 that is arranged to separate the biological substance from substances having a higher molecular weight than the biological substance.

The separation process of the full bioreactor contents must be completed within a number of hours for reasons of cell viability.

An element of this invention is the repeated discontinuous fed batch cell culturing between the exponential growth phase and the early stationary growth phase in alternating bioreactors. This process gives high biological substance yields in a relatively short period compared to perfusion processing thanks to the low levels of waste components. In addition the repeating of this short but high yield phase of the fed batch process makes much higher overall yields possible compared to regular batch and fed batch processing. The overall yield of biological substance can accumulate up to 25× that of regular batch processing within 10 days after the first fed batch culture has reached the early stationary phase.

An additional advantage of this discontinuous repeated fed batch cell culturing is the option to make continuous downstream processing possible thanks to the short intervals between the consecutive harvestings (0.5-2 days). Biological substance can be continuously tapped from an intermediate storage vessel for feed of the further purification. By processing in this way high product yields can be realized in a low volume continuous operational mode.

The invention claimed is:

1. A method for the production of a proteinaceous biological substance by culturing mammalian cells that produce said biological substance in a bioreactor, said method comprising:

a) providing a bioreactor with a cell culture comprising said mammalian cells suspended in a culture medium; and b) performing at least one culture and harvest cycle comprising incubating said cell culture in said bioreactor until the cell culture has reached the exponential phase or the early stationary phase; and when said exponential phase or the early stationary phase is reached, harvesting the culture medium with the proteinaceous biological substance in a harvest system that functions by separating the cells from the culture medium containing the biological substance by flowing the cell culture into a centrifuge that maintains the cells as a concentrated fluidized bed through the continuous balanced action of centrifugal and fluid flow forces, whereby the fluid flow force is applied by the inflow of fresh medium whereby the cells and culture medium are separated; and (c) feeding essentially all cells back into a different bioreactor for continued culture together with fresh culture medium.

2. A method according to claim 1, comprising at least 2 culture and harvest cycles.

3. A method according to claim 1, wherein during incubation of the cell culture at least part of the cell culture is continuously flowed into a separation system that comprises a size selective semipermeable membrane, wherein the membrane separates the cells and the proteinaceous biological substance from substances having a lower molecular weight than the proteinaceous biological substance, thereby creating a cell- and biological substance-free effluent that is outputted and a cell- and biological substance-containing fluid stream that is fed back into the bioreactor, and wherein loss of said effluent is at least compensated by feeding culture medium or a component thereof into the bioreactor.

4. A method according to claim 2, wherein the cell culture incubations in culture and harvest cycles subsequent to said at least one culture and harvest cycle are performed in different or alternating bioreactors.

5. A method according to claim 1, wherein said cells are CHO cells.

6. A method according to claim 1, wherein said proteinaceous biological substance is an antibody or antigen binding fragment thereof.

7. A method according to claim 1, wherein said cells are cultured in a fed-batch culture system.

8. A method according to claim 1, wherein the volume of the cell culture exceeds the capacity of the harvest system.

* * * * *